(12) United States Patent
Keller

(10) Patent No.: US 9,072,504 B2
(45) Date of Patent: Jul. 7, 2015

(54) BONE SEPARATOR

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 88 days.

(21) Appl. No.: 13/037,073

(22) Filed: Feb. 28, 2011

(65) Prior Publication Data

US 2011/0152955 A1 Jun. 23, 2011

Related U.S. Application Data

(63) Continuation of application No. 10/567,966, filed as application No. PCT/EP2005/003576 on Apr. 5, 2005, now Pat. No. 7,927,337.

(30) Foreign Application Priority Data

Apr. 19, 2004 (DE) .......................... 10 2004 018 872

(51) Int. Cl.
*A61B 17/70* (2006.01)
*A61B 17/02* (2006.01)

(52) U.S. Cl.
CPC ............. *A61B 17/025* (2013.01); *A61B 17/708* (2013.01); *A61B 2017/0256* (2013.01)

(58) Field of Classification Search
CPC ............... A61B 17/025; A61B 17/708; A61B 2017/0256
USPC ............. 606/53–55, 57–59, 90, 105; 403/154
See application file for complete search history.

(56) References Cited

U.S. PATENT DOCUMENTS

| 4,427,918 | A | | 1/1984 | Lipp |
| 4,475,546 | A | | 10/1984 | Patton |
| 4,611,586 | A | * | 9/1986 | Agee et al. ...................... 606/55 |
| 4,827,918 | A | * | 5/1989 | Olerud .......................... 606/258 |
| 4,957,495 | A | | 9/1990 | Kluger |
| 6,036,691 | A | | 3/2000 | Richardson |

(Continued)

FOREIGN PATENT DOCUMENTS

| DE | 4201043 | 7/1993 |
| JP | 2001-1129108 | 5/2001 |

(Continued)

OTHER PUBLICATIONS

International Preliminary Report on Patentability directed to counterpart International Patent Application No. PCT/EP2005/003576 dated Nov. 14, 2006.

(Continued)

*Primary Examiner* — Pedro Philogene
*Assistant Examiner* — David Comstock
(74) *Attorney, Agent, or Firm* — Jonathan Spangler; Marjorie Jarvis

(57) ABSTRACT

A bone spreader includes two tubular pin holders which are connected to one another by a parallel guide system, and two pins that are configured to be connected to the bone parts that are to be spread apart. In order to give the bone parts that are to be spread apart a more secure position in relation to one another, at least one of the pin holders is provided with a locking device for a pin located in the pin holder. This locking device includes a locking finger which is movable tangentially with respect to the pin holder and which, in the locking position, engages in a transverse groove of the associated pin and can be formed by a pivotably mounted hook.

6 Claims, 1 Drawing Sheet

(56) References Cited

U.S. PATENT DOCUMENTS

| | | |
|---|---|---|
| 6,340,363 B1 | 1/2002 | Bolger et al. |
| 6,729,515 B2 | 5/2004 | Nicosia et al. |
| 7,011,658 B2 | 3/2006 | Young |
| 2003/0187436 A1 | 10/2003 | Bolger et al. |

FOREIGN PATENT DOCUMENTS

| | | |
|---|---|---|
| SU | 1463250 | 3/1989 |
| SU | 1630494 A1 | 2/1997 |
| WO | WO 03/024344 A1 | 3/2003 |

OTHER PUBLICATIONS

Notification of Reasons for Refusal in counterpart Japanese Patent Application No. 2007/507698 dated Sep. 14, 2010. English translation attached.

* cited by examiner

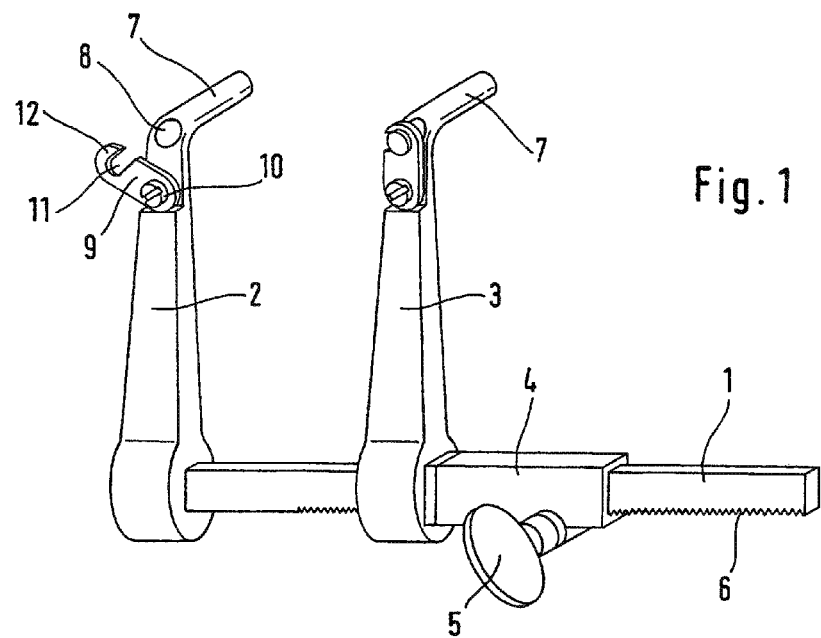
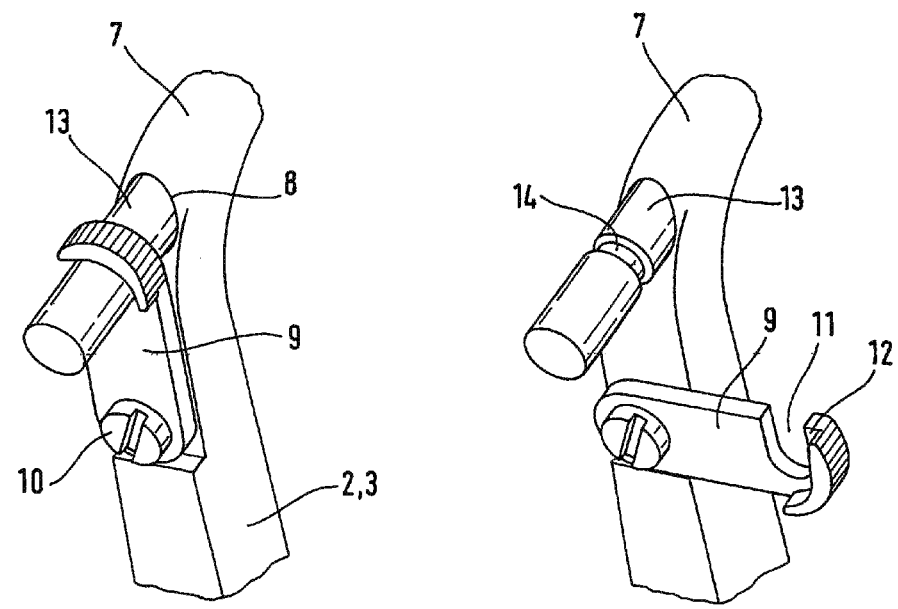

BONE SEPARATOR

FIELD AND BACKGROUND OF THE INVENTION

The invention relates to a bone spreader for spreading bone parts apart including two parallel tubular pin holders, which are connected to one another by a parallel guide system, and two pins to be connected to the bone parts that are to be spread apart. In connection with the invention, this term also includes screws. The pins are introduced parallel to one another into the bone parts that are to be spread apart. Their free sections are introduced into the pin holders. When these are now moved away from one another or moved closer to one another by means of the parallel guide system, this movement is transmitted to the bone parts. This type of spreader is especially suitable for distraction of two cervical vertebral bodies for the purpose of implantation of a cervical intervertebral prosthesis, as the vertebral bodies are guided parallel to one another during the distraction. However, this parallel attribute applies only with respect to the direction of the pin holders. Two degrees of freedom remain. These are, on the one hand, a rotation of the bone parts about the pin axis, which for various reasons is of no consequence in normal circumstances, and, on the other hand, a displacement in the direction of the pin holders, which displacement can be prevented by a locking device. For this purpose, a first known design of this locking device, disclosed in WO03/024344, uses a friction clamp, which in many cases is not secure enough. A second known design, disclosed in U.S. Pat. No. 6,340,363, uses a clamping screw or some kind of clamp. A clamping screw, however, cannot be maneuvered, or may be maneuvered only with difficulty, deep within the operating site. The issue remains, furthermore, of how a clamp can be designed so that it is both secure and easy to operate.

SUMMARY OF THE INVENTION

According to the invention, this disadvantage is remedied by the fact that the locking device is designed in the form of a locking finger which is guided between a locking position and a release position in a transverse movement tangentially with respect to the pin holder and at least one transverse groove in the pin, into which groove the locking finger engages in the locking position. Several transverse grooves may also be provided, one of which is chosen for the engagement of the locking finger. To ensure that the locking finger cannot be lost as a separate part, according to a further feature of the invention, it is designed as a hook which is mounted so as to be pivotable about an axis extending approximately parallel to the pin holder. The arrangement is especially simple and clear if the hook is arranged at the open end of the pin holder closer to the parallel guide system.

BRIEF DESCRIPTION OF THE DRAWINGS

The invention is explained in more detail below with reference to the drawing which depicts an advantageous illustrative embodiment and in which:

FIG. 1 shows an overall view of the spreader, and

FIGS. 2 and 3 show partial views of the spreader in different stages of its operation.

DETAILED DESCRIPTION OF THE INVENTION

A first spreader body 2 is arranged rigidly at the end of a guide bar 1 of noncircular cross section. A second spreader body 3 with a guide tube 4 is arranged parallel to the spreader body 2 on the guide bar 1 and is displaceable in the longitudinal direction of said guide bar 1, but not rotatable. The displacement is effected using a toggle 5 which is connected to a pinion (not shown) engaging in a toothing 6 of the guide bar 1. In addition, any kind of locking means can be connected to the spreader body 3 or to the guide tube 4 so as to secure the distance between the spreader bodies 2 and 3.

Arranged at the free ends of the spreader bodies 2 and 3 there are tubular pin holders 7 which are set at an angle in relation to the spreader bodies 2, 3. They extend parallel to one another in planes which are perpendicular to the guide bar. They are used for receiving two pins, each one of which is connected respectively to one of the two bones or fragments that are to be distracted. By operating the toggle 5, it is possible for these bone parts or fragments to be spread apart from one another or guided toward one another, in which process they are held parallel to one another in relation to the axes of the two pin holders 7. To this extent, the bone spreader can be regarded as being known.

Whereas in known bone spreaders of this kind the hole inside the pin holder is closed at the rear end connected to the associated spreader body 2, 3, according to the invention, it is continued right through at this location, such that it opens out at 8. Adjacent to the opening 8, a hook plate 9 is mounted pivotably by way of a screw 10. It lies in a plane extending substantially perpendicular to the axis of the pin holder. It contains a hook cutout 11 which is outwardly delimited by a hook finger 12 whose direction extends tangentially with respect to the axis of the pin holder.

The associated pins 13 have, at least at their rear end, one or more peripheral grooves 14 whose width (measured in the longitudinal direction of the pin) is slightly greater than the thickness of the plate 9 or hook finger 12. When a pin is located in the pin holder in such a way that its rear end protrudes outward at the rear, as is shown in FIG. 2, the plate 9 can be pivoted in such a way that the hook finger 12 engages in one of the grooves 14 and in this position, which is illustrated in FIG. 3, prevents the pin 13 from moving in its longitudinal direction.

The hook finger 12 can be designed such that it locks in the closed position (FIGS. 1 and 3) so as not to inadvertently come loose from here under the action of slight forces. Instead of this, or in addition, the pivot bearing of the plate 9 can be provided with a spring or catch mechanism which satisfies this purpose.

The invention has the effect that the pins received in the pin holders 7 can be secured in the pin holder by means of a rapid and simple movement by the operator. In this way, the secured bone parts are prevented from executing a relative movement in the direction of the pin holders.

The invention claimed is:

1. A bone spreader for spreading bone parts apart, comprising:
    a parallel guide system having a guide bar with a first end and a second end;
    a first spreader body arranged rigidly at the first end of a guide bar, the first spreader body having a first tubular pin holder arranged at a free end of the first spreader body and configured to be exclusively set at a rigid angle in relation to the first spreader body and to the guide bar; and
    a second spreader body arranged on the second end of the guide bar and displaceable in a longitudinal direction of the guide bar, the second spreader body having a second tubular pin holder arranged at a free end of the second spreader body and set at a rigid angle in relation to the second spreader body;

wherein the first tubular pin holder and the second tubular pin holder extend parallel to one another and perpendicular to the guide bar, wherein the first tubular pin holder and the second tubular pin holder are open at both ends to receive a first pin and a second pin therethrough.

2. The bone spreader of claim 1, wherein the displacement of the first spreader body and second spreader body is effected using a pinion that engages a toothing in the guide bar.

3. The bone spreader of claim 1, wherein the first and second tubular pin holders are configured with a locking device to secure the first pin and second pin, respectively.

4. The bone spreader of claim 3, wherein the first pin and the second pin are configured with one or more peripheral grooves for engaging the locking device.

5. The bone spreader of claim 3, wherein the locking device comprises a hook finger that extends tangentially to the first and second tubular pin holders.

6. The bone spreader of claim 3, wherein the locking device is pivotably mounted to the first and second spreader body.

* * * * *